(12) United States Patent
Yang et al.

(10) Patent No.: US 10,730,926 B2
(45) Date of Patent: *Aug. 4, 2020

(54) CHROMATOGRAPHIC METHOD FOR ISOLATING AND PURIFYING HIGH-PURITY RECOMBINED HUMAN SERUM ALBUMIN

(71) Applicant: Wuhan Healthgen Biotechnology Corp, Wuhan, Hubei (CN)

(72) Inventors: Daichang Yang, Hubei (CN); Bo Shi, Hubei (CN); Qianni Shi, Hubei (CN); Jiquan Ou, Hubei (CN); Jingru Liu, Hubei (CN)

(73) Assignee: WUHAN HEALTHGEN BIOTECHNOLOGY CORP, Hubei, Wuhan (CN)

( * ) Notice: Subject to any disclaimer, the term of this patent is extended or adjusted under 35 U.S.C. 154(b) by 19 days.

This patent is subject to a terminal disclaimer.

(21) Appl. No.: 14/653,258

(22) PCT Filed: May 9, 2013

(86) PCT No.: PCT/CN2013/075405
§ 371 (c)(1),
(2) Date: Jun. 17, 2015

(87) PCT Pub. No.: WO2014/094406
PCT Pub. Date: Jun. 26, 2014

(65) Prior Publication Data
US 2015/0329618 A1    Nov. 19, 2015

(30) Foreign Application Priority Data

Dec. 21, 2012 (CN) .......................... 2012 1 0559390

(51) Int. Cl.
*C07K 14/765* (2006.01)
*C07K 1/16* (2006.01)
*C07K 1/20* (2006.01)

(52) U.S. Cl.
CPC ................................... *C07K 14/765* (2013.01)

(58) Field of Classification Search
None
See application file for complete search history.

(56) References Cited

U.S. PATENT DOCUMENTS

| | | |
|---|---|---|
| 2,705,230 A | 3/1955 | Reid |
| 4,446,163 A | 5/1984 | Galle et al. |
| 4,754,019 A | 6/1988 | Gion et al. |
| 5,459,048 A | 10/1995 | Kuner et al. |
| 5,521,287 A | 5/1996 | Ohmura et al. |
| 5,561,115 A | 10/1996 | Tenold |
| 5,612,196 A | 3/1997 | Becquart |
| 7,193,041 B2 | 3/2007 | Perry et al. |
| 7,304,208 B2 | 12/2007 | Rodriquez et al. |
| 7,423,124 B2 | 9/2008 | Belew |
| 8,058,407 B2 | 11/2011 | Sun et al. |
| 9,023,990 B2 | 5/2015 | Yang et al. |
| 9,255,138 B2 | 2/2016 | Yang et al. |
| 9,951,100 B2 | 4/2018 | Yang et al. |
| 10,183,984 B2 | 1/2019 | Yang |
| 10,428,107 B2 | 10/2019 | Yang |
| 2001/0034053 A1 | 10/2001 | Winge |
| 2002/0127661 A1 | 9/2002 | Farwick |
| 2003/0170810 A1 | 9/2003 | Vedadi et al. |
| 2005/0214902 A1 | 9/2005 | Belew |
| 2007/0293420 A1 | 12/2007 | Schumann et al. |
| 2008/0206436 A1 | 8/2008 | Strohbehn et al. |
| 2008/0318277 A1 | 12/2008 | Huang et al. |
| 2009/0105465 A1 | 4/2009 | Arunakumari et al. |
| 2010/0031394 A1 | 2/2010 | Huang et al. |
| 2010/0047428 A1 | 2/2010 | Lejars et al. |
| 2010/0190708 A1 | 7/2010 | Tsuno et al. |

(Continued)

FOREIGN PATENT DOCUMENTS

| | | |
|---|---|---|
| CN | 1896239 | 1/2007 |
| CN | 100540667 | 1/2007 |

(Continued)

OTHER PUBLICATIONS

Ge Healthcare Capto MMC multimedia product sheets 2005: 24 pages.*
Lees, A., et al. 2009 BioProcess International: 42-48.*
He, Y., et al. 2011 PNAS 108(47): 19078-19083, and Supporting Information p. 1-8.*
Belew et al., "Purification of recombinant human serum albumin (rHSA) produced by genetically modified Pichia Pastoris," Separ Sci Tech (2008) 43:3134-3153.
Bio-Rad BioProcess International (2010), http://www.bioprocessintl.com/journal/2010/July_August/Nuvia-S-Media, retreived from Internet May 10, 2013, 4 pages.
Cabrera-Crespo et al., "Albumin purification from human placenta," Biotechnol Appl Biochem (2000) 31:101-106.
Chen et al., "Purification of recombinant human serum albumin from fermentation broth," Pharm Biotechnol (2003) 10(1):25-27 (English language abstract).

(Continued)

*Primary Examiner* — Marsha Tsay
(74) *Attorney, Agent, or Firm* — Rimon, P.C.

(57) ABSTRACT

Disclosed is a chromatographic method for isolating and purifying high-purity recombined human serum albumin, comprising: conducting cation-exchange chromatography on recombinant human serum albumin, and adding alcohol to a buffer solution to remove endotoxin, so as to obtain a primary product I; under binding conditions, conducting anion/hydrophobic composite resin exchange chromatography on the primary product I to obtain an intermediate product II; conducting hydrophobic chromatography on the intermediate product II to obtain the target product, the purified high-purity recombined human serum albumin. The purity of the recombined human serum albumin obtained by isolating and purifying with the chromatographic method of the present invention is greater than 99.9999%, and the content of the endotoxin meets the criteria stipulated by Chinese pharmacopoeia.

20 Claims, 3 Drawing Sheets

(56) References Cited

U.S. PATENT DOCUMENTS

| | | | | |
|---|---|---|---|---|
| 2011/0263834 | A1* | 10/2011 | Lees | C07K 1/16 530/399 |
| 2012/0315697 | A1 | 12/2012 | Pettit et al. | |
| 2015/0203530 | A1 | 7/2015 | Yang et al. | |
| 2018/0194801 | A1 | 7/2018 | Yang et al. | |

FOREIGN PATENT DOCUMENTS

| | | | |
|---|---|---|---|
| CN | 101665798 | 3/2010 | |
| CN | 101768206 | 7/2010 | |
| CN | 102127164 | 7/2011 | |
| CN | 102190722 | 9/2011 | |
| CN | 102532254 | 7/2012 | |
| EP | 0428758 | 5/1991 | |
| EP | 0683233 | 5/1995 | |
| WO | WO-90/15617 | 12/1990 | |
| WO | WO-2000/044772 | 8/2000 | |
| WO | WO-2004/099405 | 11/2004 | |
| WO | WO-2012/083580 | 6/2012 | |
| WO | WO 2012083580 A1 * | 6/2012 | C07K 14/765 |

OTHER PUBLICATIONS

Chinese Application No. CN-200510019084.4, filed Jul. 13, 2005, 31 pages.
Englard et al., "Precipitation Techniques," Method in Enzymology (1990) 182:285-300.
Hegyi et al., Introduction to Practical Biochemistry (2013), pp. 1-2, 89-104.
Huang et al., "Production of human serum albumin by sugar starvation induced promoter and rice cell culture," Transgenic Res (2005) 14(5):569-581.
Latta et al., "Synthesis and purification of mature human serum albumin from *E. coli*," Biotechnology (1987) 5:1309-1314.
Macro-PrepÒ HIC Support product information, 2 pages.
Mavituna "Production of recombinant human serum albumin in transgenic plants and plant cells," Dissertation, Doktorin der Naturwissenschaften (2005), pp. 1-143.
SAFC Biosciences, "Protein Purification Techniques," (2006) 1:1-2.
Saunders et al., "Secretion of human serum albumin from Baillus subtilis," J. of Bateriology (1987) 169(7):2917-2925.
He et al., "Large-scale production of functional human serum albumin from transgenic rice seeds," PNASA (2011) 108(47):19078-19083.
GE Healthcare, "Instructions 11-0035-05 AA," Capto MMC (2005) 24 pages.
Lees et al., "Purifiying a recalcitrant therapeutic recombinant protein with a mixed-mode chromatography sorbent," BioProcess International (2009) 42-48.
Office Action for U.S. Appl. No. 13/206,844, dated Jul. 16, 2013, 9 pages.
Response to Office Action for U.S. Appl. No. 13/206,844, dated Oct. 16, 2013, 7 pages.
Final Office Action for U.S. Appl. No. 13/206,844, dated Dec. 27, 2013, 17 pages.
Request for Continued Examination in U.S. Appl. No. 13/206,844, filed Apr. 28, 2014, 13 pages.
Office Action for U.S. Appl. No. 13/206,844, dated Aug. 27, 2014, 20 pages.
Response to Office Action for U.S. Appl. No. 13/206,844, dated Feb. 26, 2015, 15 pages.
Office Action for U.S. Appl. No. 13/206,844, dated Jun. 4, 2015, 18 pages.
Response to Office Action for U.S. Appl. No. 13/206,844, filed Sep. 4, 2015, 6 pages.
Notice of Allowance for U.S. Appl. No. 13/206,844, dated Oct. 1, 2015, 7 pages.
Office Action for U.S. Appl. No. 13/206,884, dated May 22, 2013, 19 pages.
Response to Office Action in U.S. Appl. No. 13/206,884, filed Aug. 22, 2013, 26 pages.
Final Office Action for U.S. Appl. No. 13/206,884, dated Oct. 25, 2013, 25 pages.
Response to Final Office Action for U.S. Appl. No. 13/206,884, filed Jan. 27, 2014, 24 pages.
Advisory Action for U.S. Appl. No. 13/206,884, dated Feb. 25, 2014, 4 pages.
Request for Continued Examination in U.S. Appl. No. 13/206,884, filed Apr. 25, 2014, 42 pages.
Notice of Allowance for U.S. Appl. No. 13/206,884, dated Jan. 2, 2015, 10 pages.
Issue Fee Payment for U.S. Appl. No. 13/206,884, filed Apr. 1, 2015, 3 pages.
Non-final Rejection for U.S. Appl. No. 14/676,727, dated Aug. 1, 2016, 19 pages.
Response to Non-final Rejection for U.S. Appl. No. 14/676,727, dated Jan. 31, 2017, 29 pages.
Final Rejection for U.S. Appl. No. 14/676,727, dated May 24, 2017, 32 pages.
Response to Final Rejection for U.S. Appl. No. 14/676,727, dated Aug. 9, 2017, 32 pages.
Advisory Action for U.S. Appl. No. 14/676,727, dated Sep. 8, 2017, 4 pages.
Notice of Appeal filed for U.S. Appl. No. 14/676,727, dated Nov. 22, 2017, 7 pages.
Pre-Brief Appeal Conference Decision for U.S. Appl. No. 14/676,727, dated Dec. 6, 2017, 2 pages.
Notice of Allowance for U.S. Appl. No. 14/676,727, dated Jan. 10, 2018, 7 pages.
International Preliminary Report on Patentability for PCT/CN2013/075405, dated Apr. 13, 2015, 15 pages (Including English Translation).
International Search Report for PCT/CN2013/075405, dated Sep. 26, 2013, 7 pages (Including English Translation).
Non-final Rejection for U.S. Appl. No. 14/996,092, dated Sep. 13, 2017, 8 pages.
Office Action for U.S. Appl. No. 15/917,529, dated Jun. 7, 2018, 21 pages.
Response to Office Action for U.S. Appl. No. 15/917,529, dated Dec. 6, 2018, 14 pages.
Terminal Disclaimer to Obviate a Double Patenting Rejection Over a "Prior" Patent for U.S. Appl. No. 15/917,529, dated Dec. 6, 2018, 3 pages.
Notice of Allowance & Examiner Initial Interview Summary for U.S. Appl. No. 15/917,529, dated Jan. 31, 2019, 17 pages.
Notice of Allowance for U.S. Appl. No. 15/917,529, dated Jun. 5, 2019, 12 pages.

* cited by examiner

CHROMATOGRAPHIC METHOD FOR ISOLATING AND PURIFYING HIGH-PURITY RECOMBINED HUMAN SERUM ALBUMIN

CROSS REFERENCES TO RELATED APPLICATIONS

This application is a U.S. national stage application of International Patent Application No. PCT/CN2013/075405, filed May 9, 2013, which claims benefit of priority to Chinese Patent Application No. CN 201210559390.7, entitled "Chromatography method for separating and purifying high purity recombinant human serum albumin," filed Dec. 21, 2012, and the contents of the above referenced applications are incorporated herein by reference in their entireties for all purposes.

FIELD OF THE INVENTION

The invention belongs to the field of biotechnology, and in particular relates to a method for isolating and purifying high-purity recombinant human serum albumin (OsrHSA) for clinical application.

BACKGROUND OF THE INVENTION

Human serum albumin (HSA) is a non-glycosylated single chain protein consisting of 585 amino acids, having a molecular weight of 66.5 kD and an isoelectric point between 4.7-4.9. It is the most abundant protein in human blood plasma, making up about 60% of the total plasma proteins. There is about 40 g of HSA in per liter of human blood. Besides being present in the plasma, HSA is also found in tissues and body secretions, skins and lymph cavities. Under normal physiological conditions of human beings, HSA has an effect of maintaining plasma colloid osmotic pressure, nourishing, accelerating the concrescence of wounds, and as a carrier, participating in transportation of many hydrophobic biological molecules such as hormones, biological active substances and drugs in the blood. Therefore, HSA is an important medical protein that is mainly used clinically for the treatment of hypoproteinemia caused by loss of blood, burn, scald, plastic surgery and brain lesion, as well as for the treatment of liver cirrhosis, hydronephrosis and so on.

At present, HSA for clinical use is mainly prepared by extracting and isolating from human plasma. However, this preparation approach has the following disadvantages: on one hand, the source of plasma is insufficient, i.e. the limited blood supply is unable to meet the demands of production of HSA and the relevant preparations thereof; on the other hand, blood itself may potentially be a risk factor, for example, it may contain dangerous infectious pathogens such as hepatitis virus, human immunodeficiency virus (HIV) and so on, which causes enormously concerns about the application of HSA extracted from plasma.

With the development of modern DNA recombinant and synthesis techniques, the researchers take a profound interest in the production and application of recombinant human serum albumin (OsrHSA). So far, people have tried to use various expression systems for mass production of OsrHSA. For example, prokaryotes such as *E. coli* (Latta, M. et al., Bio/Technology, 5:1309-1314, (1987)), *Bacillus subtilis* (Saunders, C. W. et al, J. Bacteriol. 169: 2917-2925, (1987)), eukaryotes such as yeasts (WO 00/44772, EP0683233A2, U.S. Pat. No. 5,612,196) and cultivation of animal cells have been used for the production of OsrHSA. However, such approaches are not suitable for industrial production due to low expression level or high production cost.

Chinese patent application No. 201010606635.8 of the present inventors discloses a method for extracting OsrHSA from rice. Based on the method, the present invention further studies the process for removing endotoxin from OsrHSA and improving the protein purity >99.9999%, thereby obtaining this novel technical solution of the present invention. The application No. 201010606635.8 is specifically incorporated herein and is to be used for all purposes consistent with incorporation by reference.

SUMMARY OF THE INVENTION

It is an object to provide a chromatography method for isolating and purifying high-purity recombinant human serum albumin from crude protein extract of transgenic rice seeds. The purity of the obtained recombinant human serum albumin can reach 99.9999%. The content of endotoxin meets the standards of human serum albumin stipulated in Chinese pharmacopoeia.

The technical solution of the present invention is:

A chromatography method for isolating and purifying high-purity recombinant human serum albumin (OsrHSA), comprising the following steps of:

1) subjecting crude extract of recombinant human serum albumin to cation exchange chromatography, adding an alcohol in an buffer to remove endotoxin, to obtain primary product I;

2) subjecting the primary product I to anion exchange chromatography, to obtain secondary product II;

3) subjecting the secondary product II to hydrophobic interaction chromatography, to obtain the target product, high-purity recombinant human serum albumin.

Specifically, the cation exchange chromatography is performed on a cation/hydrophobic composite resin selected from Capto-MMC or Bestarose Diamond MMC. The anion exchange chromatography is performed on an anion/hydrophobic composite resin selected from Capto-Adhere or Bestarose Diamond MMA. The hydrophobic interaction chromatography is performed on a resin selected from Phenyl Sepharose HP, Phenyl Sepharose FF, Phenyl Bestarose HP or Phenyl Bestarose FF.

Specifically, the alcohol according to the method of the present invention is selected from the group consisting of ethanol and isopropyl alcohol.

Specifically, the buffer according to the method of the present invention comprises a wash buffer, an equilibrium buffer I and an equilibrium buffer II; wherein the wash buffer comprises 10-20% alcohol by volume, the equilibrium buffer I comprises 0-10% alcohol by volume, the equilibrium buffer II comprises 5-15% alcohol by volume. Said alcohol is selected from the group consisting of monohydric alcohols and dihydric alcohols. More specifically, said alcohol is ethanol or isopropyl alcohol.

Preferably, the wash buffer comprises 15% anhydrous ethanol, and the equilibrium buffer II comprises 10% anhydrous ethanol. More preferably, the wash buffer comprises sodium acetate anhydrous 2 g/L, 15% anhydrous ethanol; the conductivity is adjusted with NaCl to 83 mS/cm, and pH is adjusted to 4.6-5.0 with acetic acid. The equilibrium buffer I comprises: sodium acetate anhydrous 2 g/L, NaCl 15 g/L, pH is adjusted to 4.2-4.8 with acetic acid. The equilibrium buffer II comprises: sodium acetate anhydrous 2 g/L, NaCl 15 g/L, 10% anhydrous ethanol, pH is adjusted to 4.2-4.8 with acetic acid.

Alternatively, preferably, the wash buffer comprises 10-16% isopropyl alcohol by volume; the equilibrium buffer II comprises 4-11% isopropyl alcohol by volume. More preferably, the wash buffer comprises sodium acetate anhydrous 2 g/L, 15-16% isopropyl alcohol; the conductivity is adjusted with NaCl to 82-89 mS/cm, pH is adjusted to 4.8-4.9 with acetic acid. The equilibrium buffer I comprises: sodium acetate anhydrous 2 g/L, NaCl 11 g/L, pH is adjusted to 4.5 with acetic acid. The equilibrium buffer II comprises: sodium acetate anhydrous 2 g/L, NaCl 15 g/L, 10-11% isopropyl alcohol, pH is adjusted to 4.5 with acetic acid.

BRIEF DESCRIPTION OF THE DRAWINGS

wherein, M: molecular mark, L: extract sample, M1: control group, M2: test group 1, M3: test group 2; FT: flow-through fraction of the loaded sample; M3FT: flow-through fraction of M3 test group, 600, 660 and 730 corresponding to the flow-through fraction of the loaded sample 600 mL, 660 mL and 730 mL, respectively; wash: impurity-washing fraction containing OsrHSA; Elution: Elution fraction containing OsrHSA.

wherein, GE-MMC: Capto-MMC; Best-MMC: Bestarose Diamond MMC; Elu: Elution fraction from primary purification performed on the two resins; M: molecular mark; FT: flow-through fraction of the loaded sample; wash: impurity-washing fraction containing OsrHSA; Elu: Elution fraction containing OsrHSA; S: extract sample; CIP1: Elution fraction of resin regeneration 1; CIP2: Elution fraction of resin regeneration 2.

wherein, CK: control group; UE: test group (10% ethanol was added in the sample and the equilibrium buffer); M: molecular mark; Load: sample; FT: flow-through fraction of the loaded sample; Elution: Collected elution fraction containing target protein under two conditions; CIP: resin regeneration.

wherein, M: molecular mark; MMC: sample; FT: flow-through fraction containing OsrHSA, CIP: resin regeneration.

wherein M: molecular mark; L: sample; FT: flow-through fraction containing OsrHSA; Elu: elution fraction containing OsrHSA; C: resin regeneration.

wherein, M: molecular mark; Ad: loaded sample; FT: flow-through fraction containing OsrHSA; CIP: resin regeneration.

wherein, Left: comparison image of SDS-PAGE of impurity detection before and after purification of human serum albumin in the rice seeds; Right: Western Blotting detection image of hybridization with full impurity antibody of rice seeds before and after purification of human serum albumin in the rice seeds; M: molecular mark.

wherein, A: Capto-MMC chromatography; B: Capto-Adhere chromatography; C: Phenyl HP chromatography; L: loaded sample; FT: flow-through fraction; W: impurity-washing fraction; Elu: elution fraction; C: CIP of resin.

wherein, A: Capto-MMC chromatography; B: Capto-Adhere chromatography; C: Phenyl HP chromatography; M: molecular mark; L: loaded sample; FT: flow-through fraction; W: impurity-washing fraction; E: elution fraction; C: CIP of resin.

DETAILED DESCRIPTION OF THE INVENTION

The characteristics and advantages of the present invention will be described in detail in conjunction with the accompanying drawings. The examples are only provided to illustrate the present invention, but not intended to limit the other content disclosed by the invention in any way.

Unless otherwise specified, the materials and reagents used in the following examples were ordinary commercially available.

[Example 1] Preparation of OsrHSA Extract

Transgenic rice containing OsrHSA was prepared according to the method of Chinese patent NO. 200510019084.4 and OsrHSA was extracted from the transgenic rice seeds according to the method of Chinese patent NO. 201010606635.8 to obtain clear OsrHSA extract.

[Example 2] Selection of Conditions for Cation Exchange Chromatography as Primary Purification Method: referring to the method of Chinese Patent Application NO. 201010606635.8; Groups: test group and control group 1. Cation Exchange Chromatography Performed on Capto MMC as Primary Purification and Process for Removing Endotoxin with Alcohol Capto MMC resin was used to perform cation exchange chromatography as primary chromatography and ethanol was added into the buffer of the test group to remove endotoxin, while no ethanol was added into the control group (M1).

Test group 1 (M2): The equilibrium buffer and the sample were added with 10% ethanol by volume, and the particular process was:

Column-packing: About 30 mL of Capto MMC resin was packed in an XK16/400 mm chromatography column, and then washed with 0.5N NaOH for 30 min to kill the pyrogens;

Equilibration: The column was equilibrated with 200 mL of equilibrium buffer (sodium acetate anhydrous 2 g/L, NaCl 15 g/L, 10% (v/v) anhydrous ethanol, pH 4.5 adjusted with acetic acid) until the pH reached 4.5 and was on the base line;

Sample-loading: The clear extract sample containing OsrHSA was added with 10% (v/v) anhydrous ethanol and 11 g/L NaCl, and NaOH was used to adjust pH to 4.5; the sample was loaded at a flow rate of 600 cm/h, and the conductivity of the sample was 20-21 mS/cm, pH was 4.5;

Re-equilibration: After sample-loading, the chromatography column was re-equilibrated with 100 mL of equilibrium buffer (sodium acetate anhydrous 2 g/L, NaCl 15 g/L, 10% (v/v) anhydrous ethanol, pH 4.5 adjusted with acetic acid, prepared with water for injection) at a flow rate of 300 cm/h;

Impurity-washing: 200 mL of wash buffer (sodium acetate anhydrous 2 g/L, NaCl 58.5 g/L, pH 4.8 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Test group 2 (M3): The equilibrium buffer and the sample were added with 10% ethanol, the impurity wash buffer was added with 20% ethanol, and the particular process was:

Column-packing: About 30 mL of Capto MMC resin was packed in an XK16/400 mm chromatography column (bed height: 21 cm), and then washed with 0.5N NaOH for 30 min to kill the pyrogens;

Equilibration: The column was equilibrated with 200 mL of equilibrium buffer (sodium acetate anhydrous 2 g/L, NaCl 15 g/L, 10% (v/v) anhydrous ethanol, pH 4.5 adjusted with acetic acid) at a flow rate of 300 cm/h until the pH reached 4.5 and was on the base line;

Sample-loading: The clear extract sample containing OsrHSA was added with 10% (v/v) anhydrous ethanol and 11 g/L NaCl, pH 4.5 adjusted with NaOH. The sample was loaded at a flow rate of 600 cm/h. The conductivity of the sample was 20-21 mS/cm, and pH was 4.5;

Re-equilibration: After sample-loading, the chromatography column was re-equilibrated with 100 mL of equilibrium buffer (sodium acetate anhydrous 2 g/L, NaCl 15 g/L, 10% (v/v) anhydrous ethanol, pH 4.5 adjusted with acetic acid, prepared with water for injection) at a flow rate of 300 cm/h;

Impurity-washing: 200 mL of wash buffer (sodium acetate anhydrous 2 g/L, NaCl 120 g/L, pH 4.8 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Figure 1:
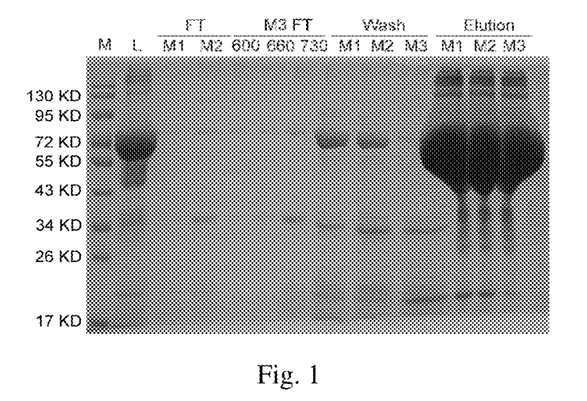
FIG. 1 shows purification efficiency and loading capacity of Capto-MMC chromatography under three different conditions.

Results: The determination results of purity and loading capacity are shown in FIG. 1. There was no obvious difference in the purity between the control group and the two experimental groups. The addition of alcohol in the wash buffer was favorable to remove the 17-26 KD purity bands. The addition of alcohol in the wash buffer did not influence the loading capacity of Capto-MMC. The FT of the three groups showed that the loading capacity of each group was above 30 mL extract/mL resin.

Endotoxin: As shown in Table 1, the addition of alcohol in the wash buffer of Capto-MMC chromatography had good removal efficiency on endotoxin. When the equilibrium buffer and extraction buffer were added with 10% (v/v) ethanol and the wash buffer was added with 20% ethanol, Capto-MMC chromatography had the best efficiency for removal of endotoxin, which was 3.6 times of the control group.

TABLE 1

Comparison of endotoxin contents of Capto-MMC chromatography containing an alcohol in the wash buffer

| Group | Extract (EU/mL) | Total EU of loaded sample | Collected fraction (EU/mL) | Total EU of collected fraction | n-fold decrease of total EU |
|---|---|---|---|---|---|
| Control group (M1) | | $3 \times 10^5$ | 400-600 | $1.25 \times 10^4$ | 24 |
| Test group 1 (M2) | 1500-2000 | $3.3 \times 10^5$ | 100-200 | $4.5 \times 10^3$ | 76 |
| Test group 2 | | $3.7 \times 10^5$ | 100-200 | $4.3 \times 10^3$ | 87 |

2. Optimization of Process for Removing Endotoxin by Capto MMC Chromatography with an Alcohol Added in the Buffer 2.1 the Removal Efficiency of Endotoxin with or without Adding an Alcohol in the Extract Sample was Compared, and the Particular Process was:

Control group 1 (M1): The equilibrium buffer and the extract sample were added with 10% ethanol, and the wash buffer was added with 20% ethanol, the particular process was:

Column-packing: About 29 mL of Capto MMC resin was packed in a BioRad 15/400 mm chromatography column, and then washed with 0.5N NaOH for 30 min to kill the pyrogens;

Equilibration: The column was equilibrated with 200 mL of equilibrium buffer I (sodium acetate anhydrous 2 g/L, NaCl 15 g/L, 10% (v/v) anhydrous ethanol, pH 4.5 adjusted with acetic acid) at a flow rate of 300 cm/h until the pH reached 4.5 and was on the base line;

Sample-loading: The clear extract solution sample containing OsrHSA was added with 10% (v/v) anhydrous ethanol and 11 g/L NaCl, pH 4.5 adjusted with NaOH; 870 mL of sample was loaded at a flow rate of 600 cm/h, and the conductivity of the sample was 20-21 mS/cm, pH was 4.5; the content of endotoxin in the sample was 1000-2000 EU/mL;

Re-equilibration: After sample-loading, the chromatography column was re-equilibrated with 100 mL of equilibrium buffer II (sodium acetate anhydrous 2 g/L, NaCl 15 g/L, 10% (v/v) anhydrous ethanol, pH 4.5 adjusted with acetic acid, prepared with water for injection) at a flow rate of 300 cm/h;

Impurity-washing: 200 mL of wash buffer (sodium acetate anhydrous 2 g/L, 20% (v/v) anhydrous ethanol, a conductivity of 83 mS/cm adjusted with NaCl, pH 4.8 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Test group (M2): Neither the extract sample nor the equilibrium buffer I were added with ethanol. After loading sample, the chromatography column was equilibrated with 150 mL of equilibrium buffer II containing 10% ethanol (about 5 CV), the wash buffer was added with 20% ethanol; the other conditions were the same as M1 group.

The results are shown in Table 2. The decrease of the total EU was basically identical in the two parallel test groups. The extract sample and equilibrium buffer with or without alcohol has no obvious effect on endotoxin removal. There was little difference in the concentration and volume of the collected fraction between the two groups, and the contents of endotoxin were the same. This further showed that the same efficiency of endotoxin removal can be achieved even there was no alcohol in the sample and equilibrium buffer I.

TABLE 2

Comparison of endotoxin of Capto-MMC chromatography when the sample and equilibrium buffer I had or had no alcohol

| Test group | Loaded sample (mL) | Total EU of loaded sample | Collected fraction (mL) | Endotoxin of collected fraction (EU/mL) | Total EU of collected fraction | n-fold decrease |
|---|---|---|---|---|---|---|
| M1 | 870 | $1.31 \times 10^6$ | 95 | 200-400 | $2.4 \times 10^4$ | 55 |
| M2 | 870 | $1.31 \times 10^6$ | 100 | 200-300 | $2.5 \times 10^4$ | 53 |

2.2 Comparison of Endotoxin Removal Efficiency when Different Amounts of an Alcohol were Added in the Wash Buffer Control Group 1 (M1):

Column-packing: About 29 mL of Capto MMC resin was packed in a BioRad 15/400 mm chromatography column, and then the column was washed with 0.5N NaOH for 30 min to kill the pyrogens;

Equilibration: The column was equilibrated with 200 mL of equilibrium buffer I (sodium acetate anhydrous 2 g/L, NaCl 15 g/L, pH 4.5 adjusted with acetic acid) at a flow rate of 300 cm/h until the pH reached 4.5 and was on the base line;

Sample-loading: The clear extract sample containing OsrHSA was added with 11 g/L NaCl, pH was adjusted to 4.5 with NaOH; 650 mL of sample was loaded at a flow rate of 600 cm/h, and the conductivity of the sample was 20-21 mS/cm, pH was 4.5, the content of endotoxin in the sample was 1000-2000 EU/mL;

Re-equilibration: After sample-loading, the chromatography column was re-equilibrated with 150 mL of equilibrium buffer II (sodium acetate anhydrous 2 g/L, NaCl 15 g/L, 10% (v/v) anhydrous ethanol, pH 4.5 adjusted with acetic acid, prepared with water for injection) at a flow rate of 300 cm/h;

Impurity-washing: 200 mL of wash buffer (sodium acetate anhydrous 2 g/L, 20% (v/v) anhydrous ethanol, a conductivity of 83 mS/cm adjusted with NaCl, pH 4.8 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Test group 1 (M2): Except that 15% (v/v) anhydrous ethanol was added in the wash buffer, the conditions were the same as M1 group.

Test group 2 (M3): Except that 10% (v/v) anhydrous ethanol was added in the wash buffer, the conditions were the same as M1 group.

The results are shown in Table 3.

TABLE 3

Comparison of endotoxin content when different amounts of alcohol were added in the wash buffer

| Test group | Total EU of loaded sample | Collected fraction (mL) | Endotoxin of collected fraction (EU/mL) | Total EU of collected fraction | n-fold decrease |
|---|---|---|---|---|---|
| M1 | $1.17 \times 10^6$ | 78 | 200-300 | $1.9 \times 10^4$ | 62 |
| M2 | $1.17 \times 10^6$ | 90 | 200-300 | $2.25 \times 10^4$ | 52 |
| M3 | $1.17 \times 10^6$ | 88 | 300-400 | $3.08 \times 10^4$ | 38 |

As shown in Table 3, the total EU of endotoxin in M3 group was 38-fold decrease, and had significant difference compared with M1 group (control group); 15% ethanol was added in M2 group, the total EU of endotoxin in M2 group was 52-fold decrease; the content of endotoxin of the collected fraction in M2 group was the same as that of M1 group and has no obvious difference compared with M1 group (control group). The concentration of ethanol in the wash buffer of MMC can be decreased to about 15%, which had no obvious influence on endotoxin removal efficiency.

2.3 Endotoxin Removal Efficiency when the Wash Buffer Contained Isopropyl Alcohol Control group (CK): Column-packing: About 29 mL of Capto MMC resin was packed in a BioRad 15/400 mm chromatography column, and then washed with 0.5N NaOH for 30 min to kill the pyrogens;

Equilibration: The column was equilibrated with 200 mL of equilibrium buffer I (sodium acetate anhydrous 2 g/L, NaCl 15 g/L, pH 4.5 adjusted with acetic acid) at a flow rate of 300 cm/h until the pH reached 4.5 and was on the base line;

Sample-loading: 900 mL of sample was loaded at a flow rate of 600 cm/h, and the conductivity of the sample was 5-8 mS/cm, pH was 4.5, the content of endotoxin in the sample was 1000-2000 EU/mL;

Re-equilibration: After sample-loading, the chromatography column was re-equilibrated with 150 mL of equilibrium buffer II (sodium acetate anhydrous 2 g/L, NaCl 15 g/L, 10% (v/v) anhydrous ethanol, pH 4.6-4.7 adjusted with acetic acid, prepared with water for injection) at a flow rate of 300 cm/h;

Impurity-washing: 200 mL of wash buffer (sodium acetate anhydrous 2 g/L, a conductivity of 82-89 mS/cm adjusted with NaCl, 15% (v/v) anhydrous ethanol, pH 4.7-4.9 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Test group 1 (M1): Column packing: About 29 mL of Capto MMC resin was packed in a BioRad 15/400 mm chromatography column, and then washed with 0.5N NaOH for 30 min to kill the pyrogens;

Equilibration: The column was equilibrated with 200 mL of equilibrium buffer I (sodium acetate anhydrous 2 g/L, NaCl 15 g/L, pH 4.5 adjusted with acetic acid) at a flow rate of 300 cm/h until the pH reached 4.5 and was on the base line;

Sample-loading: 900 mL of sample was loaded at a flow rate of 600 cm/h, and the conductivity of the sample was 5-8 mS/cm, pH was 4.5, the content of endotoxin in the sample was 1000-2000 EU/mL;

Re-equilibration: After sample-loading, the chromatography column was re-equilibrated with 150 mL of equilibrium buffer II (sodium acetate anhydrous 2 g/L, NaCl 15 g/L, 4-6% (v/v) isopropyl alcohol, pH 4.6-4.7 adjusted with acetic acid, prepared with water for injection) at a flow rate of 300 cm/h;

Impurity-washing: 200 mL of wash buffer (sodium acetate anhydrous 2 g/L, 10-11% (v/v) isopropyl alcohol, a conductivity of 82-89 mS/cm adjusted with NaCl, pH 4.7-4.9 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Test group 2 (M2): Except that the equilibrium buffer II was added with 10-11% (v/v) isopropyl alcohol instead of 4-6% (v/v) isopropyl alcohol, the wash buffer was added with 15-16% (v/v) isopropyl alcohol instead of 10-11% (v/v) isopropyl alcohol, and the conductivity was reduced to 75-76 mS/cm, the conditions were the same as that of M1 group.

The results are shown in Table 4.

TABLE 4

Comparison of endotoxin removal efficiency when isopropyl alcohol was added in the wash buffer

| Group | Total EU of loaded sample | Collected fraction (mL) | Endotoxin of collected fraction (EU/mL) | Total EU of collected fraction | n-fold decrease |
|---|---|---|---|---|---|
| CK | $8.9 \times 10^5$ | 110 | 100-200 | $1.7 \times 10^4$ | 52 |
| M1 | $7.2 \times 10^5$ | 110 | 10-20 | $1.6 \times 10^3$ | 450 |
| M2 | $8.0 \times 10^5$ | 112 | 5-10 | $1.1 \times 10^3$ | 710 |

As shown in Table 4, the total EU of endotoxin in the control group was 52-fold decrease, and that of M1 group and M2 group were 450-fold and 710-fold decrease, respectively. The removal efficiency of endotoxin was significantly improved compared to the process that ethanol was added in wash buffer. In M2 group, 15% (v/v) isopropyl alcohol was added, and the content of endotoxin was 710-fold decrease, the endotoxin removal efficiency of which was comparable to that of M1 group. This demonstrated that the amount of isopropyl alcohol added in the equilibrium buffer could be 4-11% (v/v), the amount of isopropyl alcohol added in the wash buffer could be 10-16% (v/v), and there was no obvious effect on endotoxin removal when the conductivity was in the range of 75-89 mS/cm.

3. Selection of Chromatography Resin for Cation Exchange Chromatography and the Removal Efficiency of Endotoxin with an Alcohol Added in the Wash Buffer 3.1 Bestarose Diamond MMC was Used to Perform Cation Exchange Chromatography, and Endotoxin was Removed by Adding an Alcohol in the Buffer. The Particular Process was:

Column-packing: About 33 mL of Bestarose Diamond MMC resin was packed in a BioRad 15/400 mm chromatography column, and then washed with 0.5N NaOH for 30 min to kill the pyrogens;

Equilibration: The column was equilibrated with 200 mL of equilibrium buffer I (sodium acetate anhydrous 2 g/L, NaCl 15 g/L, pH 4.5 adjusted with acetic acid) at a flow rate of 300 cm/h until the pH reached 4.5 and was on the base line;

Sample-loading: The extract solution sample containing OsrHSA was added with 11 g/L NaCl, pH was adjusted to 4.5 with NaOH; 600 mL of sample was loaded at a flow rate of 600 cm/h, and the conductivity of the sample was 20-21 mS/cm, pH was 4.5, the content of endotoxin in the sample was 1500-2000 EU/mL;

Re-equilibration: After sample-loading, the chromatography column was re-equilibrated with 150 mL of equilibrium buffer II (sodium acetate anhydrous 2 g/L, NaCl 15 g/L, 10% (v/v) anhydrous ethanol, pH 4.5 adjusted with acetic acid, prepared with water for injection) at a flow rate of 300 cm/h;

Impurity-washing impurity: 200 mL of wash buffer (sodium acetate anhydrous 2 g/L, 15% (v/v) anhydrous ethanol, a conductivity 83 mS/cm adjusted with NaCl, pH 4.8 adjusted with acetic acid, prepared with water for injection) was used to elute the impurities at a flow rate of 300 cm/h;

Elution: Elution buffer (sodium dihydrogen phosphate 2.67 g/L, disodium hydrogen phosphate 2.82 g/L, NaCl 23.4 g/L, pH 6.3-6.4, prepared with water for injection) was used to elute the target protein, obtaining the fraction containing OsrHSA.

Figure 2:
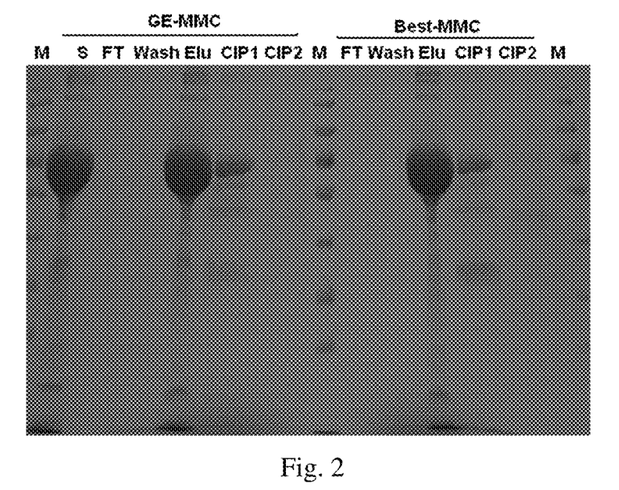
FIG. 2 shows the comparison of purity of primary purification performed on Capto MMC and Bestarose Diamond MMC.

Results: As shown in FIG. 2, purity was no obvious difference between Bestarose Diamond MMC and Capto-MMC resins. This demonstrated that Bestarose Diamond MMC can be replaced of Capto-MMC for the primary purification of OsrHSA.

Endotoxin: After the extract sample was subjected to primary purification on Bestarose Diamond MMC resin with an alcohol added in the buffer, the total EU of endotoxin was 62-fold decrease, achieving the same endotoxin removal efficiency as Capto-MMC resin.

3.2 Cation Exchange Chromatography Performed on UNO Sphere S and Process of Endotoxin Removal with an Alcohol Added in the Buffer Control group (CK): referring to the method of the Chinese Patent CN 201010606635.8 of the present inventors. The loaded sample was 400 mL.

Test group (UE), the particular process was:

Column-packing: About 18 mL of UNO Sphere S resin was packed in a BioRad 15/200 mm chromatography column, and then washed with 0.5N NaOH for 30 min to kill the pyrogens;

Equilibration: The column was equilibrated with 100 mL of equilibrium buffer (sodium acetate anhydrous 2 g/L, 10% (v/v) anhydrous ethanol, pH 4.5 adjusted with acetic acid) at a flow rate of 300 cm/h until the pH reached 4.5 and was constant;

Sample-loading: The extract solution sample containing rHSA was added with 10% (v/v) anhydrous ethanol, pH was adjusted to 4.5 with acetic acid; 400 mL of the sample was loaded at a flow rate of 300 cm/h, and the content of endotoxin in the sample was 800-1000 EU/mL;

Re-equilibration: After sample-loading, the chromatography column was re-equilibrated with 60 mL of equilibrium buffer at a flow rate of 300 cm/h;

Elution: Elution buffer (anhydrous sodium acetate 2 g/L, NaCl 14.6 g/L, pH 5.5 adjusted with acetic acid, prepared with water for injection) was used to elute the target protein, obtaining the fraction containing OsrHSA.

Figure 3:
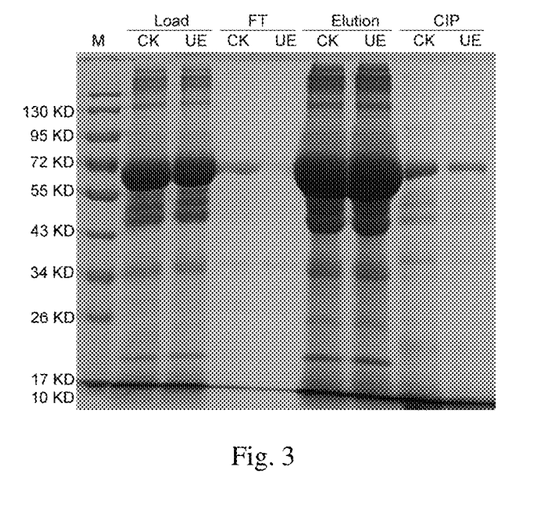
FIG. 3 shows the comparison of purification efficiency of UNO Sphere S chromatography with or without adding alcohol.

Results: As shown in FIG. 3, purity was no obvious difference between UNO Sphere S control group and the alcohol addition group. That is, UNO Sphere S resin chromatography by adding an alcohol can be used for the primary purification.

Endotoxin: After the extraction sample was subjected to primary purification on UNO Sphere S resin with alcohol addition, the decrease of the total EU of endotoxin was the same as that of the control group. This demonstrated that the alcohol in the wash buffer cannot enable UNO Sphere S to have stronger endotoxin removal efficiency. This may be relevant to the matrix of UNO Sphere S resin itself, and both Capto-MMC and Bestarose Diamond MMC resins have complex multifunctional ligands and have weak cation exchange and hydrophobic property.

[Example 3] Selection of Conditions for Anion Exchange Chromatography as Intermediate Purification 1. Under OsrHSA flow-through conditions (i.e., under the conditions of the conductivity of 40 mS/cm and pH 7.0, OsrHSA flowed through instead of binding to the resin, while the impurities bond to the resin, and thus OsrHSA was separated from the impurities). Anion exchange chromatography was performed on Capto-Adhere and Bestarose Diamond MMA.

About 40 mL of Capto-Adhere resin was packed in an XK16×400 mm chromatography column, and the packing height was 20.5 cm. The column was equilibrated with about 8 CV of equilibrium buffer (25 mM PB, NaCl 23.4 g/L, pH7.0) until UV, pH and conductivity reached the baseline. The elution buffer sample obtained from Capto-MMC or Bestarose Diamond MMC chromatography was adjusted to pH 7.0, and 288 mL of the sample was loaded at a flow rate of 300 cm/h. When the ultraviolet absorption value of flow-through fraction was >20 mAU, the target fraction containing OsrHSA was collected. The sample was taken from each 20 mL of fraction to monitor the loading capacity and the total amount of the sample when the purity of the flow-through fraction was not obviously changed; the actual loading capacity of each milliliter of Capto-Adhere resin at a flow rate of 300 cm/h was calculated.

Under the same OsrHSA flow-through conditions as Capto-Adhere, the parallel test was performed on Bestarose Diamond MMA resin to compare the purification effect and loading capacity.

Figure 4:
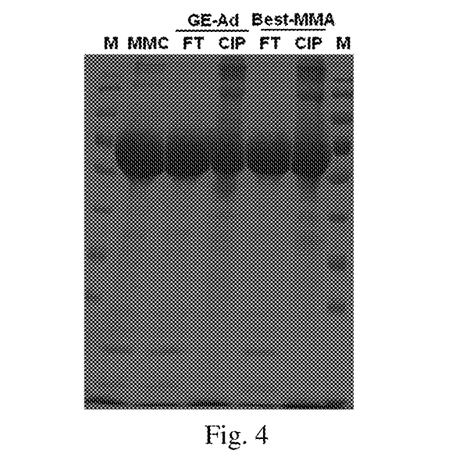
FIG. 4 shows the comparison of SDS-PAGE of the secondary purification performed on Capto-Adhere and Bestarose Diamond MMA under flow-through conditions.

Under the OsrHSA flow-through conditions, after the secondary purification with the two anion resins, HPLC purity of the target protein can reach above 98%. As shown in FIG. 4, there was no significant difference on purity between the two resins.

2. Anion Change Chromatography Performed on Capto-Adhere Resin Under OsrHSA-Binding Conditions OsrHSA-binding conditions mean that the target protein first bond to the resin and part of impurities flowed through the column, and then the target protein was eluted through particular salt and pH, to achieve the effect of separation and purification, and enrichment of target product. The conditions included: the target protein bond to the anion exchange resin under the conditions of the conductivity of 20 mS/cm and pH of 7.0-7.5, and then the target protein was eluted under the conditions of the conductivity of 40 mS/cm and pH of 7.0-7.2 to remove the impurities and enrich the target protein.

About 22 mL of Capto-Adhere resin was packed in a BioRad 15/200 mm chromatographic column, and then the column was equilibrated with 220 mL of equilibrium buffer (sodium dihydrogen phosphate 1.0 g/L, disodium hydrogen phosphate 5.0 g/L, NaCl 5.0 g/L, pH 7.5-7.6) at a flow rate of 300 cm/h until the pH reached 7.5-7.6 and stable. The elution fraction sample from Capto-MMC or Bestarose Diamond MMC chromatography was diluted with water to reach a conductivity of 19-21 mS/cm, and the pH was adjusted to 7.0 with NaOH. 150 mL of the sample was loaded at a flow rate of 300 cm/h. The column was re-equilibrated with 100 mL of equilibrium buffer. The target protein was eluted with the elution buffer (sodium dihydrogen phosphate 1.5 g/L, disodium hydrogen phosphate 5.0 g/L, NaCl 23.4 g/L, pH 7.1-7.2) at a flow rate of 300 cm/h, collecting the fraction containing OsrHSA. The content of endotoxin in the collected fraction was 100-200 EU/mL.

Under the same OsrHSA-binding conditions as Capto-Adhere resin, the parallel test was performed on Bestarose Diamond MMA resin to compare the purification effect and loading capacity.

Figure 5:
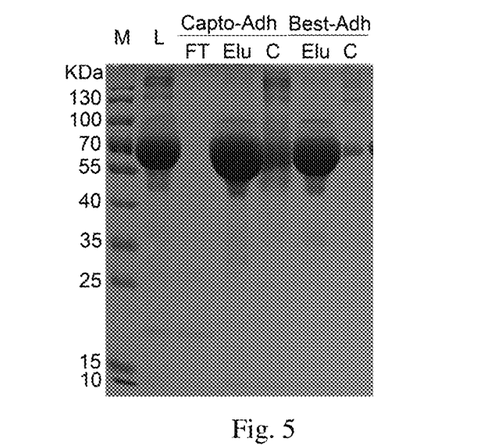
FIG. 5 shows the comparison of the secondary purification performed on Capto-Adhere and Bestarose Diamond MMA under binding conditions.

Under the OsrHSA-binding conditions, after secondary purification with Capto-Adhere resin or Bestarose Diamond MMA resin, the purity of the target protein could reach above 99.9% (ELISA detection results). Bestarose Diamond MMA resin and Capto-Adhere resin have the same purification efficiency. The electrophoretograms are shown in FIG. 5.

3. Selection of Chromatography Conditions for Anion Exchange Chromatography Performed on Capto-Adhere and Bestarose Diamond MMA By the parallel comparison of two resins of Bestarose Diamond MMA and Capto-Adhere, it was found that under the same conditions, the two resins had the substantially identical purification efficiency and loading capacity on the elution fraction obtained from the secondary purification performed on Capto-MMC or Bestarose Diamond MMC resin, demonstrating that both the two anion exchange chromatography resins can be used for the secondary purification.

The loading capacity of the two resins was higher under OsrHSA flow-through conditions than that of OrsHSA-binding conditions. The loading capacity of the former was about 25 mg sample/mL resin, while the loading capacity of the latter was about 20 mg sample/mL resin. However, the purification efficiency under OrsHSA-binding conditions was better than that under OsrHSA flow-through conditions. The purity of the former can reach above 99.9%, and the purity of the latter was only 98-99%.

Under OrsHSA-binding conditions, the two resins had better endotoxin removal efficiency than flow-through conditions. Under OsrHSA flow-through conditions, most of the endotoxin flowed through the column together with OsrHSA, resulting in a poorer endotoxin removal efficiency. But under OrsHSA-binding conditions, part of free endotoxin flowed through, and another part of endotoxin bond to the resin tightly so that OsrHSA can be selectively eluted, resulting in a better endotoxin removal efficiency.

Taking various factors into consideration, it is preferable to use the OrsHSA-binding conditions as the chromatography conditions of the two anion exchange resins, Capto-Adhere and Bestarose Diamond MMA.

Figure 6:
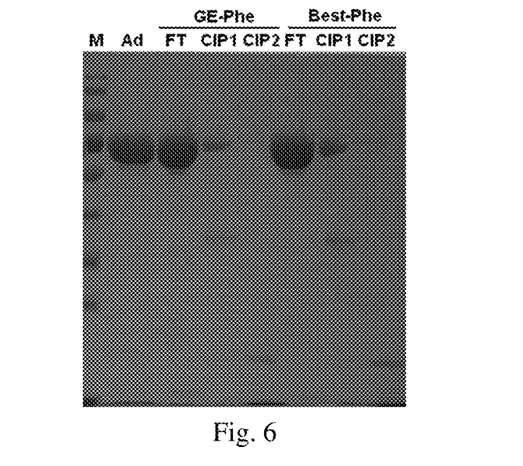
FIG. 6 shows the comparison of hydrophobic interaction chromatography performed on Phenyl Sepharose HP and Phenyl Bestarose HP as the final purification.

[Example 4] Selection of Conditions for Hydrophobic Chromatography as Final Purification 1. Hydrophobic Chromatography Performed on Phenyl Sepharose HP Referring to the method of Chinese patent CN201010606635.8 of the present applicant, about 28 mL of Phenyl sepharose HP resin was packed in a 20 XK16/200 mm chromatography column, and the column was equilibrated with 150 mL of equilibration buffer (anhydrous acetic acid sodium 2.32 g/L, sodium dihydrogen phosphate 2.81 g/L, sodium octanoate 2 g/L, ammonium sulfate, 66 g/L, pH6.5) at a flow rate of 100 cm/h. 100 mL of the elution fraction containing OsrHSA obtained from Capto-Adhere or Bestarose Diamond MMA chromatography was added with ammonium sulfate to adjust the conductivity to 75 mS/cm, and then added with 0.15 g of sodium caprylate, and then adjust pH to 6.5 with hydrochloric acid. It was loaded on the column at a flow rate of 100 cm/h. The flow-through was collected to obtain the fraction containing OsrHSA. The fraction samples were taken to determine the loading capacity and calculate the actual loading capacity of the sample from secondary purification per millilitre resin. The electrophoretogram is shown in FIG. 6.

2. Hydrophobic Chromatography Performed on Phenyl Bestarose HP

Figure 7:
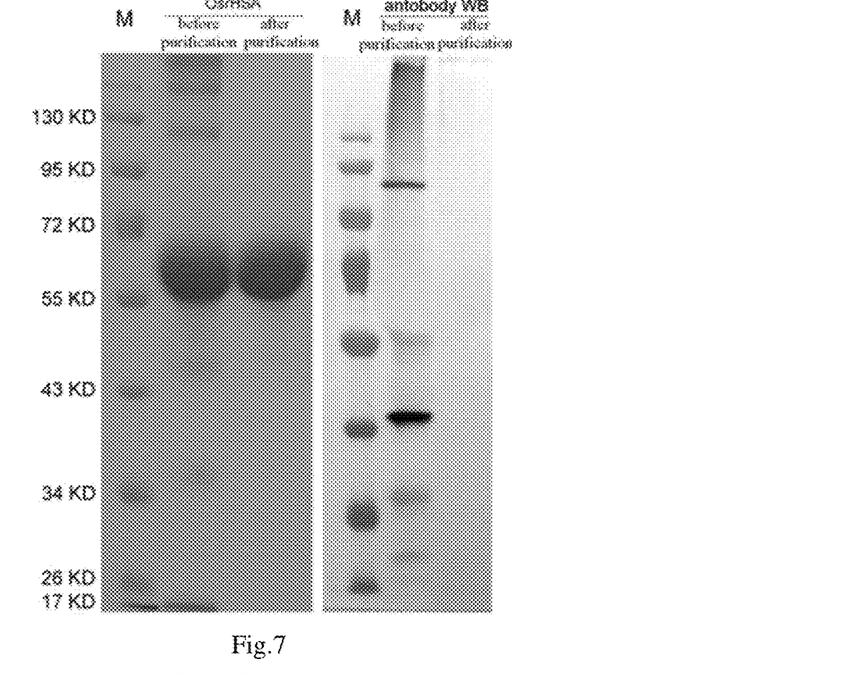
FIG. 7 shows the image of impurity detection before and after the protein purification in the rice seeds.

About 24 mL of Phenyl Bestarose HP resin was packed in an XK16/200 mm chromatography column. Parallel test was carried out according to the above method mentioned in 1 of this example. The electrophotograms are shown in FIGS. 6 and 7.

Results and Analysis:

After the fraction sample obtained from secondary purification with Capto-Adhere or Bestarose Diamond MMA was subjected to hydrophobic interaction chromatography with Phenyl Sepharose HP or Phenyl Bestarose HP, the purity of target protein could reach 99.9999% (by ELISA). The impurity proteins in the rice seed were not detected. The two hydrophobic resins had no significant difference on purity. The endotoxin contents of the fractions containing OsrHSA obtained from hydrophobic interaction chromatography performed on the two resins were less than 0.06 EU/mg. The results showed that both Phenyl Sepharose HP and Phenyl Bestarose HP hydrophobic chromatography resin can be used for the final purification of OsrHSA, and can achieve a better purification and endotoxin removal.

[Example 5] Purification of Recombinant Human Serum Albumin

Figure 8:
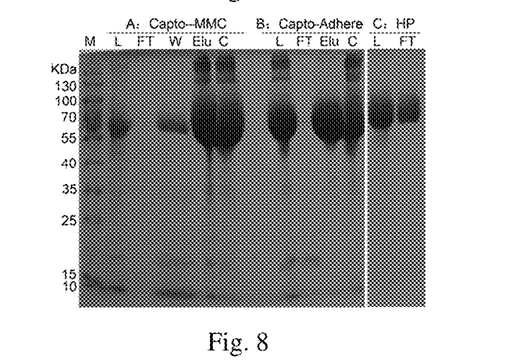
FIG. 8 shows the SDS-PAGE image of the purified OsrHSA according to one example of the present invention.

Cation exchange chromatography as primary purification: About 400 mL of Capto MMC resin was packed in an XK50/400 mm chromatography column and then washed with 0.5N NaOH for 30 min to kill the pyrogens. The chromatography column was equilibrated with 2 L of equilibration buffer I (anhydrous acetic acid sodium 2 g/L, NaCl 11 g/L, pH 4.5 adjusted with acetic acid) at a flow rate of 300 cm/h, until pH reached 5.0 and was stable. 10 L of sample was loaded on the column, and the sample had a conductivity of 20.3 mS/cm and pH of 4.8. After sample-loading, the chromatography column was re-equilibrated with 2 L of equilibration buffer II (anhydrous acetic acid sodium 2 g/L, NaCl 15 g/L, 10-11% (v/v) anhydrous ethanol, pH 4.8 adjusted with acetic acid, prepared by water for injection) at a flow rate of 300 cm/h. The impurities were eluted with 3000 mL of wash buffer (anhydrous acetic acid sodium 2 g/L, 16% (v/v) anhydrous ethanol, a conductivity of 83.5 mS/cm adjusted with NaCl, pH 5.0 adjusted with acetic acid, prepared with water for injection) at a flow rate of 300 cm/h. The target protein was eluted with the elution buffer (sodium dihydrogen phosphate 2.67 g/L, disodium hydrogen phosphate 2.82 g/L, NaCl 23.4 g/L, pH 6.3-6.4, prepared with injectable water) to obtain the fraction containing OsrHSA. The electrophotograms are shown in FIG. 8A.

Anion/hydrophobic composite resin used for exchange chromatography as secondary purification: About 68 mL of Capto-Adhere resin was packed in an XK26/200 mm chromatography column. The column was equilibrated with 600 mL of equilibration buffer (sodium dihydrogen phosphate 1.0 g/L, disodium hydrogen phosphate 5.0 g/L, NaCl 5.0 g/L, pH 7.5-7.6) at a flow rate of 300 cm/h, until the pH reach 7.5-7.6 and was stable. 500 mL of sample was loaded on the column at a flow rate of 300 cm/h. The column was re-equilibrated with about 200 mL of the equilibration buffer, and then eluted with elution buffer (sodium dihydrogen phosphate 1.5 g/L, disodium hydrogen phosphate 5.0 g/L, NaCl 23.4 g/L, pH7.1-7.2) at a flow rate of 300 cm/h, to collect the fraction containing OsrHSA. The content of endotoxin of the collected fraction was 100-200 EU/mL. The electrophotograms are shown in FIG. 8B.

Hydrophobic chromatography as final purification: About 15 mL of Phenyl sepharose HP resin was packed in an XK16/200 mm chromatography column. The column was equilibrated with 100 mL of equilibration buffer (anhydrous acetic acid sodium 2.32 g/L, sodium dihydrogen phosphate 2.81 g/L, sodium caprylate 2 g/L, ammonium sulfate 66 g/L, pH 6.5) at a flow rate of 100 cm/h. 100 mL of the elution fraction containing OsrHSA obtained from Capto-Adhere chromatography was added with ammonium sulfate to adjust the conductivity to 75 mS/cm, then added with 0.15 g of sodium caprylate, hydrochloric acid to adjust pH to 6.5. The sample was loaded at a flow rate of 100 cm/h. The flow-through was collected as the fraction containing OsrHSA. The content of endotoxin was less than 0.08 EU/mg, and the purity of the target protein was more than 99.9999%. The electrophotograms are shown in FIG. 8C.

[Example 6] Purification of Recombinant Human Serum Albumin

Figure 9:
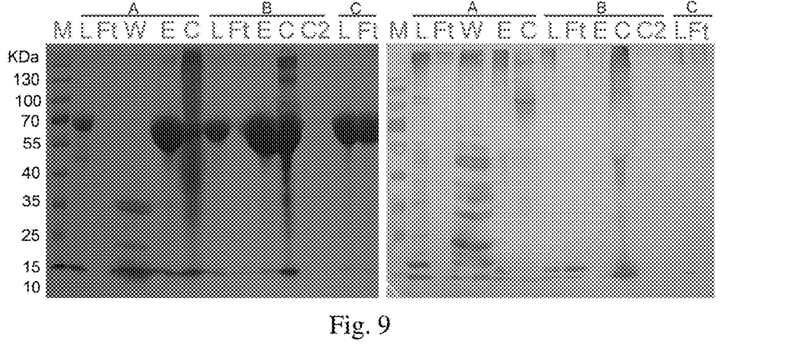
FIG. 9 shows the SDS-PAGE image (Left) and the corresponding Western Blot image (Right) of the purified OsrHSA according to another example of the present invention.

About 400 mL of Capto MMC resin was packed in an XK50/400 mm chromatography column, and then washed with 0.5N NaOH for 30 min to kill the pyrogens. The chromatography column was equilibrated with 2000 mL of equilibration buffer I (anhydrous acetic acid sodium 2 g/L, NaCl 11 g/L, pH 4.5 adjusted with acetic acid) at a flow rate of 300 cm/h, until pH reached 4.5 and was stable. 10000 mL of sample with a conductivity of 5.5-8.0 mS/cm and a pH of 4.5 was loaded on the column. After sample-loading, the chromatography column was re-equilibrated with 2000 mL of equilibration buffer II (anhydrous acetic acid sodium 2 g/L, NaCl 15 g/L, 10-11% (v/v) isopropyl alcohol, pH 4.5 adjusted with acetic acid, prepared by injectable water) at a flow rate of 300 cm/h. The impurities were eluted with 3000 mL of wash buffer (anhydrous acetic acid sodium 2 g/L, 15-16% (v/v) isopropyl alcohol, a conductivity of 82-89 mS/cm adjusted with NaCl, pH 4.8-4.9 adjusted with acetic acid, prepared with water for injection) at a flow rate of 300 cm/h. The target protein was eluted with elution buffer (sodium dihydrogen phosphate 2.67 g/L, disodium hydrogen phosphate 2.82 g/L, NaCl 23.4 g/L, pH 6.3-6.4, prepared with water for injection) to obtain the fraction containing OsrHSA. The electrophotograms are shown in FIG. 9A.

Anion/hydrophobic composite resin used for chromatography as secondary purification: About 68 mL of Capto-Adhere resin was packed in an XK26/200 mm chromatography column. The column was equilibrated with 600 mL of equilibration buffer (sodium dihydrogen phosphate 1.0 g/L, disodium hydrogen phosphate 5.0 g/L, NaCl 5.0 g/L, pH 7.5-7.6) at a flow rate of 300 cm/h, until the pH reach 7.5-7.6 and was stable. 500 mL of sample was loaded on the column at a flow rate of 300 cm/h. The column was re-equilibrated with about 200 mL of the equilibration buffer, and then eluted with wash buffer (sodium dihydrogen phosphate 1.5 g/L, disodium hydrogen phosphate 5.0 g/L, NaCl 23.4 g/L, pH 7.1-7.2) at a flow rate of 300 cm/h, to collect the fraction containing OsrHSA. The content of endotoxin of the collected fraction was 100-200 EU/mL. The electrophotograms are shown in FIG. 9B.

Hydrophobic chromatography as final purification: About 15 mL of Phenyl sepharose HP resin was packed in an XK16/200 mm chromatography column. The column was equilibrated with 100 mL of equilibration buffer (anhydrous acetic acid sodium 2.32 g/L, sodium dihydrogen phosphate 2.81 g/L, sodium caprylate 2 g/L, ammonium sulfate 66 g/L, pH 6.5) at a flow rate of 100 cm/h. 100 mL of the elution fraction containing OsrHSA obtained from Capto-Adhere chromatography was added with ammonium sulfate to adjust the conductivity to 75 mS/cm, then added with 0.15 g of sodium caprylate, pH 6.5 adjusted with hydrochloric acid, loaded at a flow rate of 100 cm/h. The flow-through was collected as the fraction containing OsrHSA. The content of endotoxin was less than 0.08 EU/mg, and the purity of the target protein was more than 99.9999%. The electrophotograms are shown in FIG. 9C.

What is claimed is:

1. A method for isolating and purifying high-purity recombinant human serum albumin, sequentially comprising the steps of:
   1) equilibrating a cation/hydrophobic composite resin for cation exchange chromatography with an equilibrium buffer I comprising about 0% to about 10% alcohol by volume;
   2) loading a crude extract of recombinant human serum albumin to the cation/hydrophobic composite resin after step 1);
   3) re-equilibrating the cation/hydrophobic composite resin after step 2) with an equilibrium buffer II comprising about 5% to about 15% alcohol by volume;
   4) washing the cation/hydrophobic composite resin after step 3) with a wash buffer comprising 10% to 16% ethanol or isopropyl alcohol by volume;
   5) eluting the cation/hydrophobic composite resin after step 4) to obtain a first product I comprising recombinant human serum albumin;
   6) subjecting the first product I to anion exchange chromatography to obtain a second product II, wherein the anion exchange chromatography is performed on an anion/hydrophobic composite resin; and
   7) subjecting the second product II to hydrophobic chromatography to obtain high-purity recombinant human serum albumin,
   wherein the recombinant human serum albumin obtained in step 7 has a purity of more than 99.9999% by HPLC, and
   the recombinant human serum albumin obtained in step 7 has a content of an endotoxin less than 0.08 EU/mg.

2. The method of claim 1, wherein the alcohol in step 1 and 3 is selected from ethanol and isopropyl alcohol.

3. The method of claim 1, wherein the wash buffer comprises 15% anhydrous ethanol by volume, and the equilibrium buffer II comprises 10% anhydrous ethanol by volume.

4. The method of claim 1, wherein the wash buffer comprises 2 g/L sodium acetate anhydrous and 15% anhydrous ethanol by volume.

5. The method of claim 1, wherein the equilibrium buffer I comprises 2 g/L sodium acetate anhydrous and 15 g/L NaCl.

6. The method of claim 1, wherein the equilibrium buffer II comprises 2 g/L sodium acetate anhydrous, 15 g/L NaCl, and 10% anhydrous ethanol by volume.

7. The method of claim 1, wherein the wash buffer comprises 10-16% isopropyl alcohol by volume, and the equilibrium buffer II comprises 4-11% isopropyl alcohol by volume.

8. The method of claim 7, wherein the wash buffer comprises 15-16% isopropyl alcohol by volume, and the equilibrium buffer II comprises 10-11% isopropyl alcohol by volume.

9. The method of claim 7, wherein the wash buffer comprises 2 g/L sodium acetate anhydrous, and 15-16% isopropyl alcohol by volume.

10. The method of claim 7, wherein the equilibrium buffer I comprises 2 g/L sodium acetate anhydrous and 11 g/L NaCl.

11. The method of claim 7, wherein the equilibrium buffer II comprises 2 g/L sodium acetate anhydrous, 15 g/L NaCl, and 10-11% isopropyl alcohol by volume.

12. The method of claim 4, wherein the conductivity of the wash buffer is adjusted with NaCl to 83 mS/cm, and the pH of the wash buffer is adjusted to 4.6-5.0 with acetic acid.

13. The method of claim 5, wherein the pH of the equilibrium buffer I is adjusted to 4.2-4.8 with acetic acid.

14. The method of claim 6, wherein the pH of the equilibrium buffer II is adjusted to 4.2-4.8 with acetic acid.

15. The method of claim 9, wherein the conductivity of the wash buffer is adjusted with NaCl to 82-89 mS/cm, and the pH of the wash buffer is adjusted to pH4.8-4.9 with acetic acid.

16. The method of claim 10, wherein the pH of the equilibrium buffer I is adjusted to 4.5 with acetic acid.

17. The method of claim 11, wherein the pH of the equilibrium buffer II is adjusted to 4.5 with acetic acid.

18. The method of claim 1, wherein the cation/hydrophobic composite resin is selected from the group consisting of Capto-MMC and Bestarose Diamond MMC.

19. The method of claim 1, wherein the anion/hydrophobic composite resin is selected from the group consisting of Capto-Adhere and Bestarose Diamond MMA.

20. The method of claim 1, wherein the hydrophobic chromatography is performed on a resin selected from the group consisting of Phenyl Sepharose HP, Phenyl Sepharose FF, Phenyl Bestarose HP, and Phenyl Bestarose FF.

* * * * *